(12) United States Patent
Spink

(10) Patent No.: US 11,793,398 B2
(45) Date of Patent: Oct. 24, 2023

(54) MEDICAL DEVICE FOR THE OBSERVATION OF A PARTLY FLUORESCENT OBJECT, USING A FILTER SYSTEM WITH A TRANSMISSION WINDOW

(71) Applicant: LEICA INSTRUMENTS (SINGAPORE) PTE. LTD., Singapore (SG)

(72) Inventor: Roger Spink, Balgach (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 18/047,455

(22) Filed: Oct. 18, 2022

(65) Prior Publication Data
US 2023/0055764 A1 Feb. 23, 2023

Related U.S. Application Data

(63) Continuation of application No. 16/303,685, filed as application No. PCT/SG2017/050267 on May 24, 2017, now Pat. No. 11,517,188.

(30) Foreign Application Priority Data

May 30, 2016 (EP) .................................. 16171887

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00186* (2013.01); *A61B 1/0646* (2013.01);
(Continued)

(58) Field of Classification Search
None
See application file for complete search history.

(56) References Cited

U.S. PATENT DOCUMENTS 4,105,333 A * 8/1978 Kaule .................. G01N 21/645
250/365
6,110,106 A * 8/2000 MacKinnon ........... A61B 5/415
600/181
(Continued)

FOREIGN PATENT DOCUMENTS

CH 526789 A 8/1972
DE 19513350 A1 10/1995
(Continued)

*Primary Examiner* — Peter D Le
(74) *Attorney, Agent, or Firm* — Hodgson Russ LLP

(57) ABSTRACT

The invention relates to a medical device for the observation of a partly fluorescent object such as tissue comprising at least one fluorophore. The fluorophore absorbs light in at least one spectral excitation waveband and emits fluorescent light in at least one spectral emission waveband. In order to be able to observe also non-fluorescent regions in the tissue without complicated filter arrangement, the medical device according to the invention comprises at least one filter system which comprises, in a filter plane, comprises a filter area and a transmission window. The filter area comprises a band pass filter having at least one passband comprising the at least one excitation waveband. The transmission window has a passband which is wider than the passband of the filter area and is cross-shaped. The at least one filter system is configured to simultaneously receive light through the filter area and the entire transmission window.

14 Claims, 7 Drawing Sheets

Figure 1:
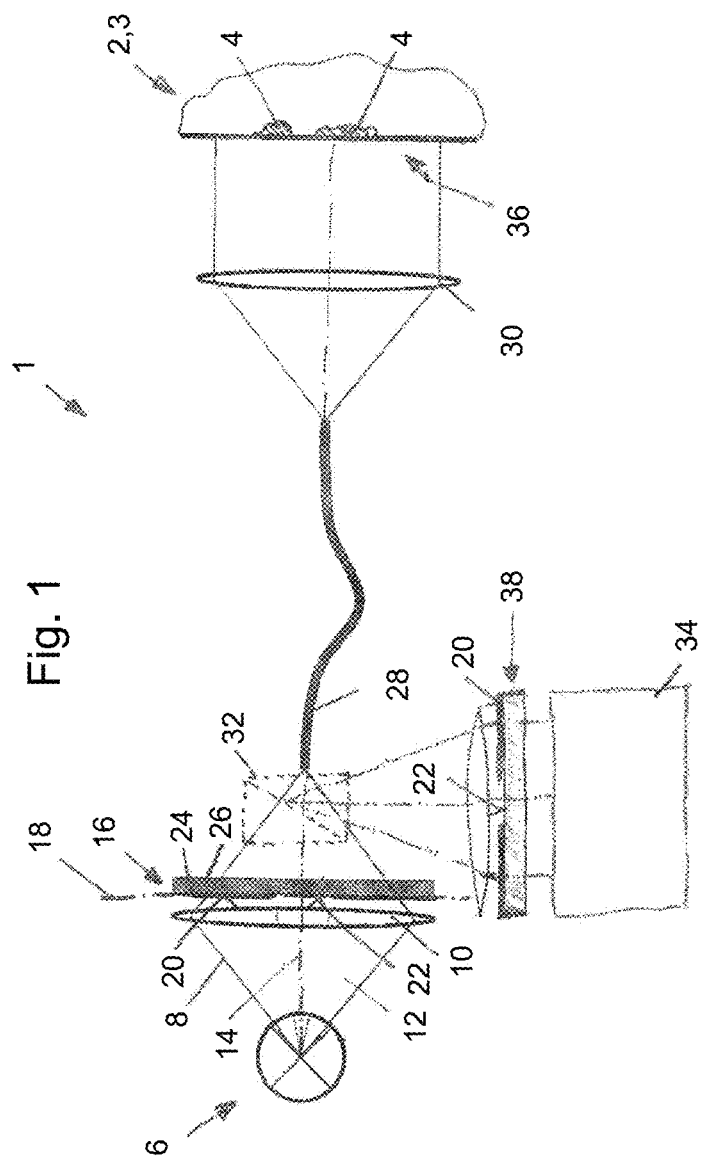

(51) Int. Cl.
*A61B 1/06* (2006.01)
*G01N 21/64* (2006.01)
*G02B 23/24* (2006.01)
G02B 21/06 (2006.01)
G02B 26/00 (2006.01)
G02B 26/02 (2006.01)

(52) U.S. Cl.
CPC ..... *G01N 21/6458* (2013.01); *G02B 23/2461* (2013.01); *G01N 2021/6471* (2013.01); *G02B 21/06* (2013.01); *G02B 26/008* (2013.01); *G02B 26/023* (2013.01)

(56) References Cited

U.S. PATENT DOCUMENTS

| | | | |
|---|---|---|---|
| 6,355,570 B1 | 3/2002 | Nakata et al. | |
| 6,747,280 B1* | 6/2004 | Weiss | G02B 21/16 |
| | | | 250/459.1 |
| 7,330,749 B1* | 2/2008 | Bhunachet | A61B 5/0071 |
| | | | 600/478 |
| 9,175,831 B2* | 11/2015 | Yamano | A61B 1/0669 |
| 2001/0033374 A1* | 10/2001 | Hoyt | G01N 21/6452 |
| | | | 356/417 |
| 2002/0001075 A1* | 1/2002 | Tsien | G01N 33/48728 |
| | | | 356/72 |
| 2002/0020819 A1 | 2/2002 | Wolleschensky et al. | |
| 2002/0022768 A1* | 2/2002 | Utsui | A61B 1/0669 |
| | | | 600/178 |
| 2002/0044212 A1 | 4/2002 | Hashimoto | |
| 2002/0062061 A1 | 5/2002 | Kaneko et al. | |
| 2002/0085293 A1* | 7/2002 | Stuckey | G02B 21/06 |
| | | | 359/368 |
| 2002/0094685 A1 | 7/2002 | Nakata et al. | |
| 2002/0141050 A1* | 10/2002 | Tafas | G02B 21/34 |
| | | | 359/368 |
| 2002/0175993 A1* | 11/2002 | Ueno | A61B 1/0638 |
| | | | 348/68 |
| 2003/0139650 A1* | 7/2003 | Homma | A61B 1/0669 |
| | | | 600/181 |
| 2003/0158470 A1 | 8/2003 | Wolters et al. | |
| 2003/0228566 A1 | 12/2003 | Mao et al. | |
| 2004/0008515 A1 | 1/2004 | Brown et al. | |
| 2004/0021078 A1* | 2/2004 | Hagler | G01J 3/06 |
| | | | 250/339.13 |
| 2004/0109231 A1 | 6/2004 | Haisch | |
| 2004/0225222 A1* | 11/2004 | Zeng | G01J 3/32 |
| | | | 600/476 |
| 2005/0001176 A1* | 1/2005 | Loney | G01N 33/58 |
| | | | 250/459.1 |
| 2005/0027166 A1* | 2/2005 | Matsumoto | A61B 1/0655 |
| | | | 977/852 |
| 2005/0226611 A1 | 10/2005 | Kawaguchi | |
| 2007/0132998 A1 | 6/2007 | Tang et al. | |
| 2007/0242335 A1* | 10/2007 | Hasling | G02B 27/0994 |
| | | | 359/233 |
| 2008/0228037 A1 | 9/2008 | Cline et al. | |
| 2008/0290292 A1* | 11/2008 | Squirrell | G01N 21/6428 |
| | | | 250/458.1 |
| 2009/0173892 A1* | 7/2009 | Courtney | G01N 33/5005 |
| | | | 250/473.1 |
| 2009/0236541 A1 | 9/2009 | Lomnes et al. | |
| 2010/0110572 A1* | 5/2010 | Yazdanfar | G02B 26/0875 |
| | | | 359/882 |
| 2011/0205651 A1 | 8/2011 | Yamano et al. | |
| 2013/0306880 A1 | 11/2013 | Yamano et al. | |
| 2013/0338438 A1* | 12/2013 | Watanabe | A61B 1/00045 |
| | | | 600/109 |
| 2014/0066733 A1* | 3/2014 | Saito | A61B 1/0646 |
| | | | 600/339 |
| 2014/0148680 A1 | 5/2014 | Kasamatsu et al. | |
| 2014/0202247 A1* | 7/2014 | Kasamatsu | H01S 3/105 |
| | | | 372/15 |
| 2016/0069807 A1 | 3/2016 | Hatanaka et al. | |

FOREIGN PATENT DOCUMENTS

| | | |
|---|---|---|
| JP | 2003307609 A | 10/2003 |
| JP | 2005031420 A | 2/2005 |
| JP | 3795233 B2 | 7/2006 |
| WO | 20110027712 A1 | 3/2011 |
| WO | 2016039000 A1 | 3/2016 |

* cited by examiner

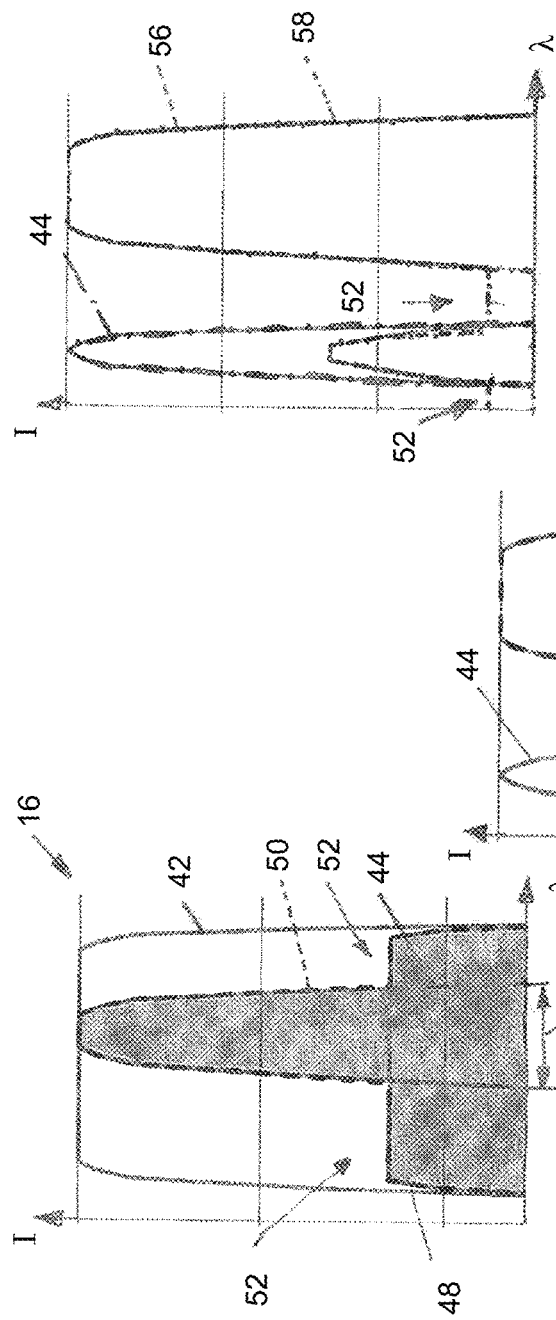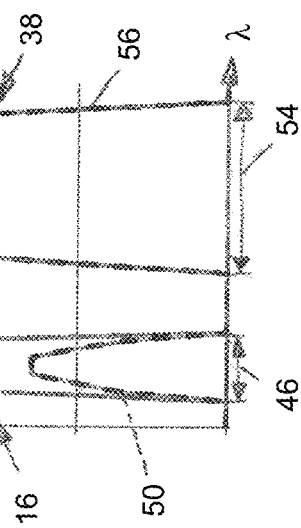

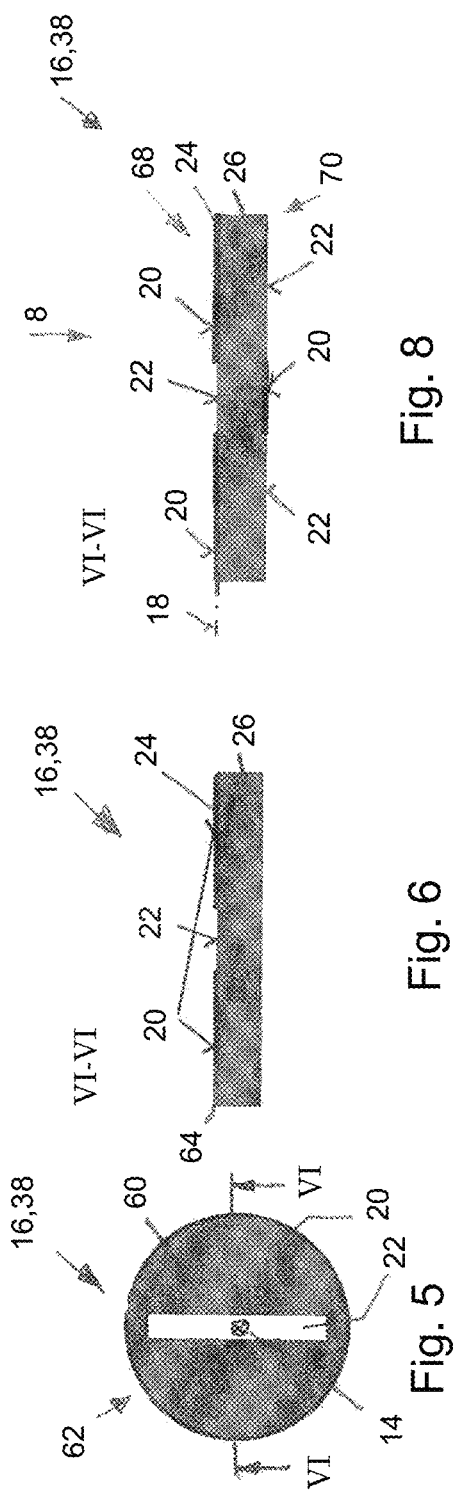
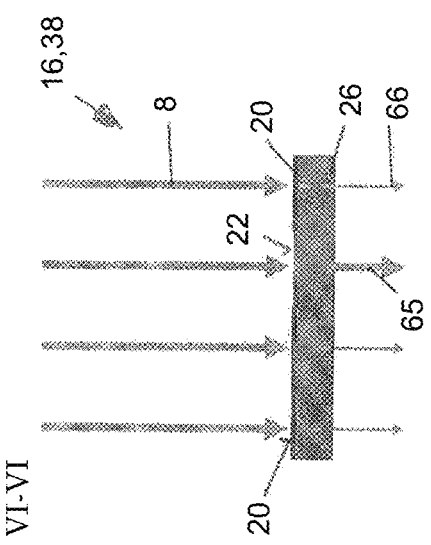

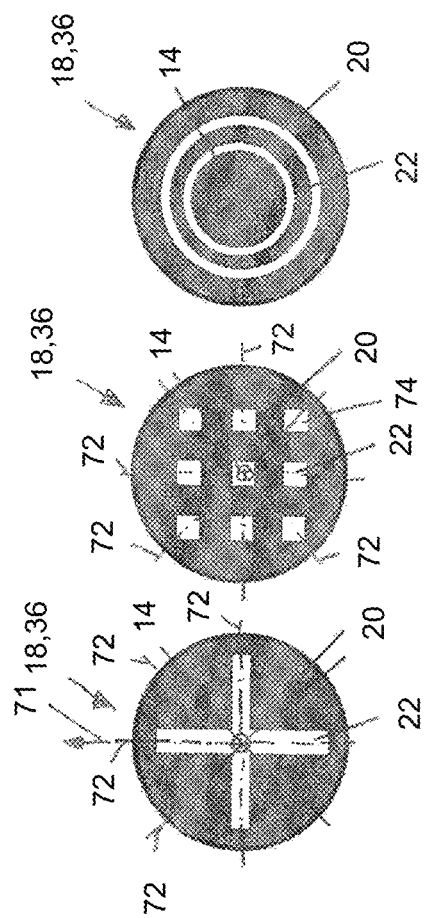

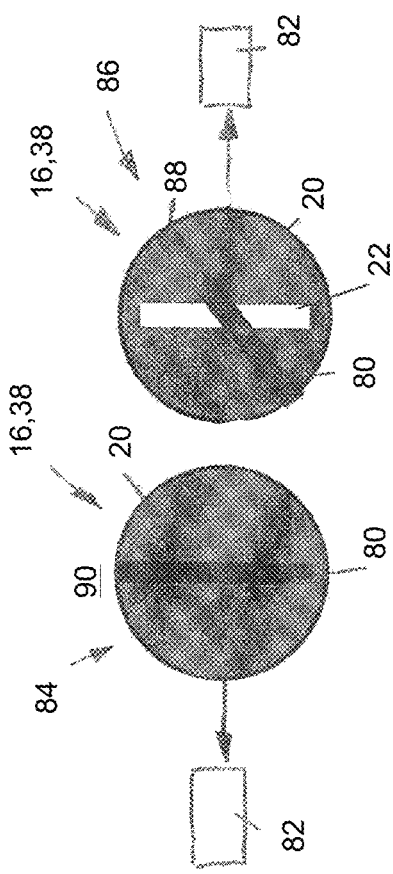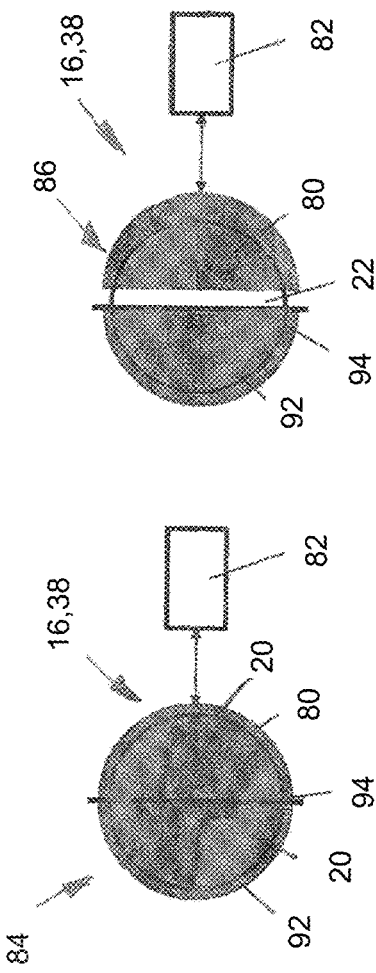

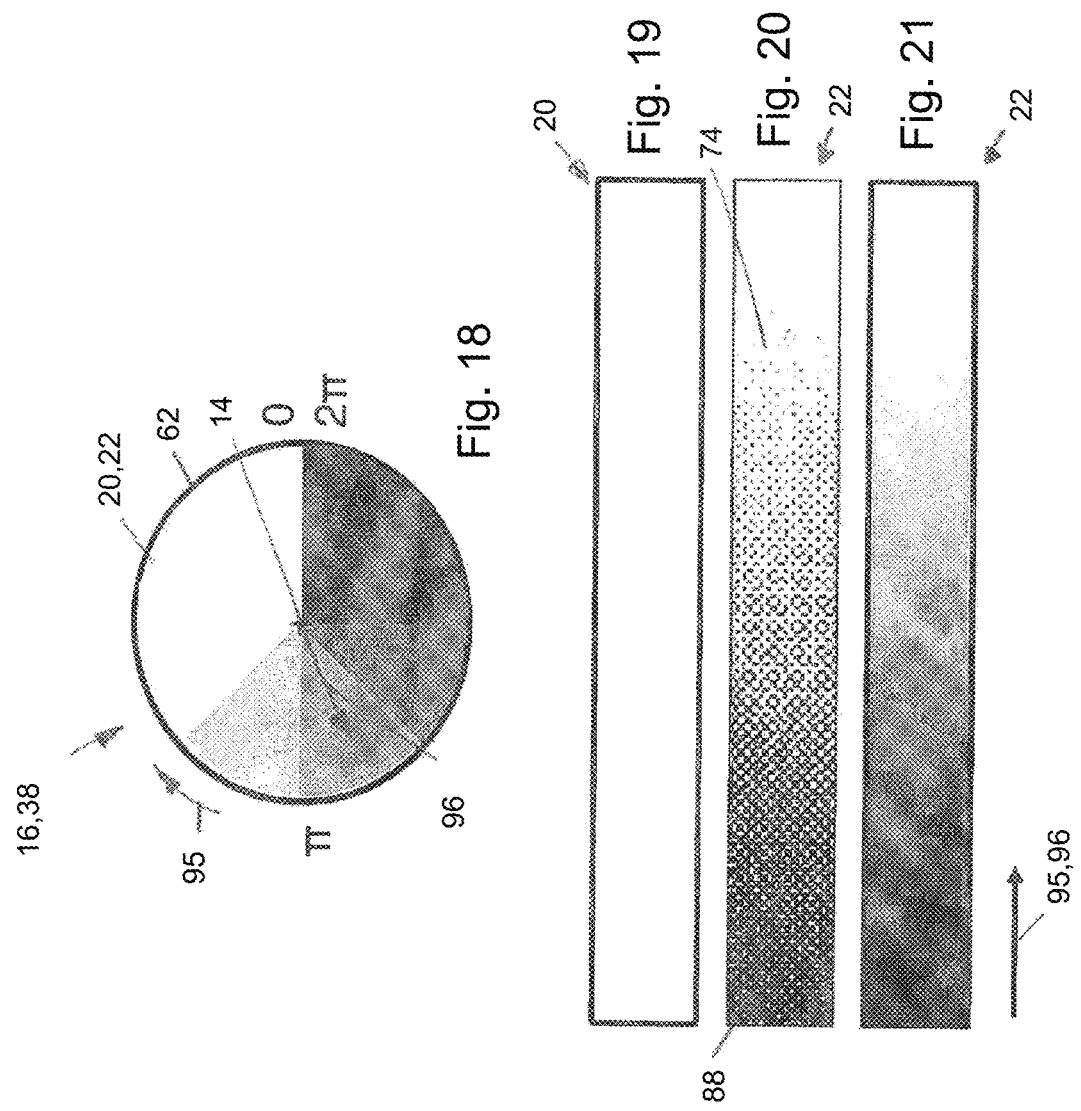

MEDICAL DEVICE FOR THE OBSERVATION OF A PARTLY FLUORESCENT OBJECT, USING A FILTER SYSTEM WITH A TRANSMISSION WINDOW

CROSS-REFERENCE TO RELATED APPLICATIONS

The present application is a continuation of U.S. application Ser. No. 16/303,685, filed on Nov. 21, 2018, which is the U.S. national phase of International Application No. PCT/SG2017/050267 filed May 24, 2017, which claims priority of European Application No. 16171887.9 filed May 30, 2016, the entire disclosures of which are incorporated herein by reference.

FIELD OF THE INVENTION

The invention relates to a medical device for the observation of a partly fluorescent object, such as tissue comprising at least one fluorophore, the fluorophore absorbing light in at least one spectral excitation waveband and emitting fluorescent light in at least one spectral emission waveband.

BACKGROUND OF THE INVENTION

Medical devices of such a type, for example microscopes and endoscopes are known. Typically, the excitation waveband and the emission waveband are separated from each other in such devices. Thus, areas which do not have a fluorophore and thus are not fluorescing, are typically dark and thus not easy to observe. The fluorophore may have been added to the tissue or be a natural part of the tissue.

It is known in the prior art to observe non-fluorescing areas by allowing the excitation light spectrum and the observation spectrum to overlap and to use the spectral overlap for crosstalk observation. The disadvantage of this solution is that there is only a narrow band observation in the region of the spectral overlap. Further, the light intensity is difficult to control as complex filter arrangements are necessary which are usable only for a specific application. A change of application requires a complete change of the filter characteristics.

SUMMARY OF THE INVENTION

It is therefore the object of the present invention to provide a medical device which allows the observation of non-fluorescent areas of tissue in an otherwise fluorescent environment by avoiding the above drawbacks.

According to the invention, the medical device as initially described comprises at least one filter system, the filter system being arranged in a filter plane, wherein, in the filter plane, the filter system comprises a filter area comprising a band pass filter having at least one passband, the passband comprising at least one of the excitation waveband and the emission waveband, and a transmission window, which is separate from the filter area, the transmission window having a passband which is wider than the passband of the filter area.

This simple solution avoids the usage of a complex filter arrangement by using a transmission window together with a filter area in the filter plane. The transmission window allows passage of a wider range of light and thus either allows illumination or viewing the non-fluorescent regions of the tissue.

The invention also relates to the use of a filter system as described above in a medical device such as a microscope or endoscope. Further, the invention relates to such a filter system configured to be fitted into the medical device.

The invention may be further improved by the following features, which may be combined independent of one another and wherein each feature has its own advantageous technical effect.

According to one embodiment, the passband of the transmission window extends on both sides of the spectrum beyond the passband of the filter area. This allows passage of both higher and lower frequencies of light and thus illumination and/or observation of the non-fluorescent regions in a larger range of colors. The wavebands, in which light is allowed to pass by the transmission window that otherwise would be blocked by the filter area, are termed sidebands in the following.

The transmission window may be a longpass filter, a shortpass filter or a filter, which does not have any colour attenuation in the visible-light range, such as a grey filter. The passband of the transmission window preferably comprises the whole visible-light range.

The transmission window may be an area in the filter plane, where at least one filter layer or filter material, which is present in the filter area, is missing.

The filter system is preferably located in an optical path of the medical device, such as the optical path of a light source and/or the optical path of a viewer system, where the viewing system may comprise an ocular, such as a monocular or binocular, and/or at least one camera, such as a colour camera, an NIR camera, a multispectral camera, a hyperspectral camera or a 3D-arrangement of such a camera or cameras.

The filter plane extends substantially perpendicular to an optical axis of the medical device at the location of the filter plane. The filter system itself may form an aperture, which limits the light transmitted through the filter system in the filter plane.

The area of the transmission window is preferably shaped to have a homogeneous illumination either of the object or at the viewing system. At least one of the filter area and the transmission window may be comprised of disconnected regions. For example, at least one of the filter area and the transmission window may be comprised of concentric rings or of an array of circular and/or polygonal regions.

To aid in the homogeneous illumination, it is preferred that at least one of the filter area and the transmission window has symmetry about at least one radial direction, the radial direction passing through the optical axis of the medical device in the filter plane. If the transmission window and/or the filter area is constituted by a multitude of separate regions, it is preferred that each of the areas exhibits a symmetry about at least one axis. For example, the filter area and/or the transmission area, or the regions making up the transmission area and/or the filter area, may be polygonal or circular. A polygonal area may in particular be slot-like, i.e. have the shape of an elongated rectangle. An array of circular or polygonal, e.g. rectangular or square, regions is also possible.

According to another embodiment, the filter system may comprise a substrate, through which the optical path and the optical axis of the medical device passes. The substrate may be glass or any other material that transmits light at low dispersion over a wide spectrum including preferably the visible-light range and the NIR range. The filter area may be located on at least one surface of the light-transmissive substrate as a filter layer.

The substrate in one embodiment has two opposing surfaces, which are preferably arranged perpendicular to the optical axis. On each of the two opposing surfaces, a filter area and a transmission window may be arranged. This allows to further limit and/or control the amount of light transmitted through the filter system. For a particularly effective limitation of light which is transmitted directly through the transmission window, the filter area on one of the two opposing surfaces may be located opposite the transmission window on the other one of the two opposing surfaces, wherein the transmission window is preferably directed towards the incident light.

The filter area on the one of the two opposing surfaces may be congruent to the transmission window on the other one of the two opposing surfaces. Thus, the filter area shadows exactly the transmission window on the other one of the two opposing surfaces so that the light transmitted through the transmission window may not pass the filter system directly.

In another embodiment, the filter system may comprise at least one moveable filter element, the moveable filter element comprising at least one of the filter area and the transmission window. The moveable filter element may be supported shiftably, pivotably and/or rotatably by the medical device. The moveable filter element may be configured to be moved from a first position relative to the optical axis, in which a larger portion of the optical path is covered, to a second position, in which a smaller portion of the optical path is covered than in the first position. In another embodiment, the surface area of the transmission window, which area is exposed to incident light, may be larger in the second position than in the first position. In particular, the exposed area of the transmission window may be reduced to zero or there might be no transmission window present in the first position. The moveable filter element allows to adapt the amount of light transmitted through the filter area and/or the transmission window by moving the filter element, and thus to adjust the amount of light transmitted in the sidebands in addition to the passband.

The filter system may, for example, comprise at least two separate filter elements in the filter plane. All filter elements may be moveable, or at least one filter element may be stationary with respect to the optical axis. The at least one moveable filter element may be configured to be moved away from the at least one stationary filter element, or the moveable filter elements may be configured to be moved away from each other. By moving the moveable filter element away from the at least one remaining filter segment to the second position, a transmission window may be created, which thus provides the wider spectrum needed to illuminate and/or observe non-fluorescent areas of the tissue. The stationary filter element may comprise a filter area and/or a transmission window.

According to another embodiment, the moveable filter element may be a cover mask, which is relatively moveable from a first to a second position, and wherein the cover mask in the first position covers a larger part of the transmission window than in the second position. The cover mask may be at least one of opaque and exhibiting the same band-pass characteristics as the filter area, and having a narrower passband than the filter area. In this embodiment, the light transmitted through the filter system in the spectral regions outside the passband of the filter system is determined by the shadowing of the transmission window by the cover mask.

In a further embodiment, an actuator system may be provided, which is operatively coupled to the at least one movable filter element and which is adapted to drive the at least one moveable filter element from a first position to a second position. The actuator system may of course by adapted to move the moveable filter element into any other position either continuously or to a fixed but alterable set of preset positions. The actuator may comprise an electric, magnetic and/or mechanic drive, and/or a manual drive.

The transmission window does not need to cover a large area in the filter plane. It is sufficient that the light flux through the transmission window is less than 1% of the light flux through the filter system. For being able to still observe non-fluorescent regions of the tissue, it is preferred that the light flux through the transmission window is at least 0.1‰ of the light flux through the filter system.

The medical device may further comprise a light source, in particular a white-light source which also emits light in the spectral excitation waveband of the at least one fluorophore. Further, the medical device may have an observation zone and a viewing system for viewing the fluorescent tissue arranged in the observation zone. The light source may be configured to emit light in the direction of the observation zone. The filter system as described above may, in one embodiment, be arranged between the light source and the observation zone and thus act as an illumination filter system. In this embodiment, the passband of the filter area preferably includes or, more preferably, corresponds to the excitation spectrum. Thus, the filter area may block out any light that does not excite fluorescence. This avoids cross talk with the fluorescence spectrum. The transmission window in this embodiment allows part of the wider spectrum of the light source to pass the filter system. Thus, the non-fluorescent regions of the fluorescent tissue may be illuminated by the sidebands.

In an additional or cumulative embodiment, the filter system may be arranged between the observation zone and the viewing system and thus act as an observation filter system. In an observation filter system it is preferred that the passband of the filter area included or, preferably, corresponds to the emission spectrum of the at least one fluorophore. Thus, the filter area in this embodiment blocks out all wavebands which do not correspond to the fluorescence emission spectrum. The transmission window nonetheless allows light in the sidebands to pass through the filter system. This allows to observe non-fluorescent parts of the otherwise fluorescent tissue both in the excitation wavebands and the sidebands.

The filter area is not necessarily restricted to a band pass filter with a single passband. Rather, in the context of this description, a band pass filter may also comprise several passbands if more than one fluorophore is used. The passbands are then tuned to the respective excitation and/or emission spectra of the various fluorophores.

In another embodiment, the transmission window and the band pass filter may be overlapping. For example, the filter area may completely or at least predominantly be provided with the band pass filter. The band pass filter may have a high transmission in the excitation or emission waveband and/or wavebands, in particular, in the NIR infrared light. The band pass filter may extend for example the full circle, i.e. 360° around the optical axis.

The transmission window, in such an embodiment, has a transmission which varies around the optical axis.

For example, the filter system may comprise regions which block the transmission of light in the passband of the transmission window. These regions may be transparent in the passband of the band pass filter. The density of these regions in a given part of the filter area, i.e. the position of the area covered by these regions, may vary in the radial and/or the circumferential direction around the optical axis. The transmission of the transmission window in its passband depends on the density, i.e. the percentage of area covered by these regions. Each region may be regarded as a small cover mask. The area in between may be regarded as a transmission window.

The varying transmission may be effected by dithering a filter layer which stops the wavebands in the passband of the transmission window but may be transparent otherwise.

This structure can reversibly apply to the filter area as well by providing a band pass filter which has a transmission in the passband of the filter area that varies with the distance from and/or the circumferential angle around the optical axis. The passband filter may comprise regions which block light in the passband of the band pass filter. The areas between the regions may be transmissive in the passband of the passband filter. The transmission of the band pass filter is then defined by the area between the regions blocking the light in the passband of the filter area. In the following, the invention is exemplarily described with reference to the drawings. In the drawings, elements which correspond to each other with respect to their functions and/or their structure are provided with the same reference numerals. For the sake of brevity, only the differences between a subsequent embodiment and the foregoing embodiments are described. If not indicated separately, a subsequent embodiment thus shares the features of the foregoing embodiments.

Further, it is clear from the above description, that the combination of various features, which may be described in combination in the embodiments and the figures may be altered depending on the application at hand. For example, if the technical effect of a particular feature is not needed in a particular application, this feature may be omitted. Vice versa, a feature, of which the technical effect is advantageous for a particular application, may be added to the combination shown and described.

BRIEF DESCRIPTION OF THE DRAWING VIEWS

Figure 17:
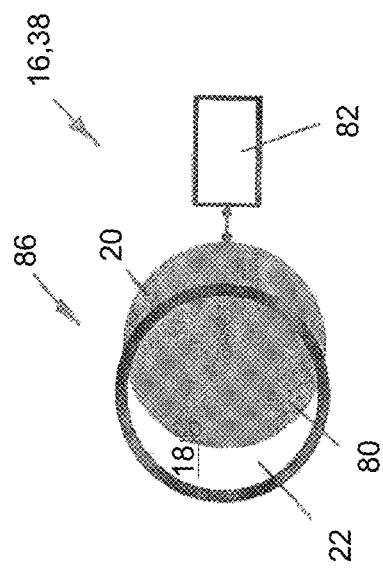
Figure 16:
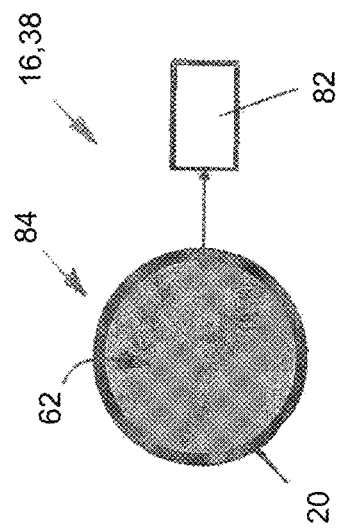

In the figures:
FIG. 1 shows a schematic representation of a medical device according to the invention;
FIG. 2 shows a schematic representation of the spectral filtering properties of a filter system of the medical system of FIG. 1;
FIG. 3 shows a schematic representation of the spectral filtering properties of a filter system of the medical system of FIG. 1;
FIG. 4 shows a schematic representation of the spectral filtering properties of a filter system of the medical system of FIG. 1;
FIG. 5 shows a schematic representation of a filter system of the medical device of FIG. 4;
FIG. 6 shows a schematic cross-section along the line VI-VI in FIG. 5;
FIG. 7 shows a schematic cut view along the line VI-VI of FIG. 5 together with incident light;
FIG. 8 shows a cut view along the line VI-VI of FIG. 5 of another embodiment;
FIG. 9-11 show schematic representations of various filter systems of the medical device shown in FIG. 1;
FIG. 12 shows a schematic representation of another embodiment of a filter system of the medical device of FIG. 1 in a first position;
FIG. 13 shows the filter system of FIG. 12 in a second position;
FIG. 14 shows a schematic representation of another embodiment of a filter system of the medical of FIG. 1 in a first position;
FIG. 15 shows the filter system of FIG. 14 in a second position;
FIG. 16 shows a schematic representation of a filter system of the medical device of FIG. 1 in a first position;
FIG. 17 shows the filter system of FIG. 16 in a second position;
FIG. 18 shows a schematic representation of another embodiment of a filter system of the medical device of FIG. 1;
FIG. 19-21 show different transmissions along the circumferential and/or radial direction of the filter system in FIG. 18.

DETAILED DESCRIPTION OF THE INVENTION

First, the structure of a medical device 1 is explained with reference to FIG. 1. The medical device can be an endoscope as shown or, alternatively, a microscope. The medical device 1 is configured to observe a partly fluorescent object 2 such as live tissue 3 which may comprise at least one fluorophore 4. The fluorophore 4 may have been added to the tissue 3 or be a natural constituent of the tissue 3. The fluorophore 4 absorbs light in an excitation waveband and emits light in an emission waveband, which preferably does not overlap the excitation waveband.

The medical device 1 may comprise a light source 6 which emits a spectrum which comprises at least the excitation wavebands but is preferably wide band and also includes a greater part if not all of the visible light range. In particular, the light source 6 may emit white light in addition to any desired excitation wavebands, which may be in the infrared.

The light 8 from the light source 6 is directed to the object 2 or the tissue 3, respectively. A diffractive element 10 such as a collimator or a lens may be arranged in an optical path 12 of the light 8. The optical path 12 extends around an optical axis 14.

The medical device 1 further comprises a filter system 16 which is arranged in a filter plane 18. As shown, the filter plane 18 may extend perpendicular to the optical axis 14.

In the filter plane 18, the filter system 16 comprises a filter area 20 and a transmission window 22. The filter area 20 comprises a band pass filter 24 having at least one passband, which comprises or, preferably, corresponds to the excitation wavebands of the at least one fluorophore 4.

The transmission window 22 covers an area in the filter plane 18 which is smaller than the area occupied by the filter area 20. In the transmission window 22, the band pass filter 24 may be absent or present in an attenuated version, e.g. by being thinner.

The band pass filter 24 may be a layer on a substrate 26. The substrate 26 is preferably a material which is transmissive at least in the excitation wavebands, preferably also in the visible light range. The substrate 26 has preferably low dispersion in the range of wavebands where it is transmissive and may be in particular a low dispersion optical glass.

The medical device 1 may further comprise an optical system 28. The optical system may include fiber optics in the case of an endoscope, or a zoom magnifying lens in the case of a microscope. The optical system 28 may comprise further diffractive elements 30, such as at least one lense for directing light onto the object 2 or the tissue 3, respectively. A beam splitter system 32 or, in the case where the optical system 28 includes fiber optics, a bundle of wave guides collecting light from the object 2 or the tissue 3, may direct light towards a viewing system 34. The viewing system 34 allows a user of the medical device 1 to inspect an observation zone 36 from which light is directed to the viewing system 34. The viewing system 34 may be an ocular, such as a monocular or binocular, or a camera, such as an infrared camera, a NIR-camera, a thermographic camera, a multispectral camera, a hyperspectral camera or a colour camera, which all may also have three dimensional capabilities.

Between the tissue 3 and the viewing system 34, another filter system 38 may be arranged, which may have the same or a different physical structure as the filter system 16. The filter system 38 in this instance may be an illumination filter system, restricting light to the excitation wavebands and to whatever additional wavebands the transmission window 22 allows to pass. The filter system 38 may be an observation filter system, which allows the emission wavebands and whatever the transmission window 22 allows to pass, to read the viewing system 34.

Next, the function of the filter system 16 and 38 is explained with reference to FIGS. 2 to 4 which show various graphs where intensity I is shown over wavelength λ of electromagnetic radiation.

In FIG. 2, the illumination spectrum 42 of the light source 6 is indicated. Further, the passband 44 of the band pass filter 24 is shown. The passband 44 corresponds to the excitation wavebands 46 of the at least one fluorophore 4.

Illuminating the band pass filter 24 with light 8 having the spectrum 42 would result in a very narrow band illumination of the tissue 3. However, by providing the transmission window 22 in which either the band pass filter 24 is missing or attenuated, or in which a band pass filter having a wider passband is located, which wider passband 44 preferably includes the illumination spectrum 42, light 8 is allowed to pass also at frequencies, which are not included in the passband 44 of the filter area. Thus, the resulting spectrum 50 of the light 8 in the optical path 12 behind the filter system 16 is indicated by the broken line 15. The intensity in the side bands 52 adjacent to the passband 44 of the filter area depends on the transmission properties of the transmission window 22 and/or its relative size with respect to the filter area 20.

FIG. 3 shows the combined effects of the filter systems 16 and 38 in medical devices for the observation of partly fluorescent tissue 3. The excitation spectrum 46 preferably does not overlap with the emission spectrum 54. The passband 44 of the filter area 20 comprises or, preferably, corresponds to the fluorescence emission spectrum 54 of the at least one fluorophore 4.

The filter system 38 in a conventional medical device 1 filters out all frequencies except those resulting from fluorescence, as shown in FIG. 3. This leaves areas of the tissue 3 where there is no fluorophore 4 and thus no fluorescence dark and hard to inspect.

By providing a transmission window 22, as shown in FIG. 4, both in the illumination filter system 16 and in the observation filter system 38, the side bands 52 are allowed to pass both the illumination filter system 16 and observation filter system 38, resulting in an observation spectrum 58 which includes the side bands 52 from the illumination spectrum 42 and the excitation wavebands 46.

FIG. 5 shows a view onto a filter system 16, 38 along the optical axis 14. The filter system 16, 38 may be supported in a frame structure 60, which may form an aperture 62 in the filter plane 18. The transmission window 22 is seen to have at least a one-axial symmetry about the optical axis 14 by forming a rectangular area.

In FIG. 6, the cross sectional view along the line VI-VI in FIG. 5 is shown. The transmission window 22 in this instance is characterized by an absence of at least one filter material or filter layer 64 which forms the band pass filter 24. Thus, the incident light can pass through the substrate 26 without any spectral attenuation. Alternatively to the situation shown in FIG. 6, the band pass filter 24 may still be present in the transmission window 22 but have smaller attenuation in the passband 44 than in the filter area 20. Alternatively or cumulatively, the transmission window 22 may be provided with a grey filter.

The effect of providing both the transmission window 22 and the filter area 20 in the filter system 16, 38 is shown in FIG. 7. The incident light 8 passes the transmission window 22 basically unfiltered, at least with significantly less attenuation than the incident light in the filter area. This is shown by the thicker arrow 65 of light being transmitted through the transmission window 22 and the comparatively thinner arrow 66 representing light from the light source 6 which has passed through the filter area 20 and is thus restricted to the passband 44.

The direct transmission of light 8 through the transmission window 22 as shown in FIG. 7 may lead to glare in some instances. To avoid this, a transmission window 22 and a filter area 20 may not only be provided on a first side 68 of the substrate 26, as in FIGS. 6 and 7, but also on a second side 70 of the substrate 26 where the first side 68 faces the incident light 8 and the second side 70 faces away from the incident light 8.

The filter area 20, which in this case may not necessarily be the same band pass filter 24 as on this first side, but may also be a light-blocking filter such as a grey filter or an opaque mask, is preferably congruent to the transmission window 22 and/or covers the transmission window completely. Thus, light which is incident perpendicular to the filter plane 18 cannot pass directly though the filter system 16, 38.

As already stated above, the actual shape and size of the transmission window 22 and the filter area 20 can vary. However, in order to obtain a homogeneous distribution of light in the observation zone 36 or the viewing system 34, a symmetric shape with respect to at least one radial direction 71 through the optical axis 14 is preferred.

The light flux through the transmission window 22 should be small in order to maintain high contrast in the fluorescence emission wavebands. In particular, the total light flux 65 through the transmission window 22 is at most 1% of the total light flux 66 through the transmission window. In another embodiment, the surface area of the transmission window 22 may comprise no more than 1% of the area of the aperture 62. To be able to observe non-fluorescent regions, the total light flux 65 may not be less than 0.1‰ of the total light flux through the filter area 20. It may be further preferred that the area of the transmission window 22 is at least 0.1‰ of the area of the aperture 62.

In FIG. 9, the transmission window has four axes of symmetry 72 by being cross-shaped. Of course, other shapes such as circular may also be used.

The transmission window 22 may be comprised of separate transmission regions 74, which are preferably arranged in an array which also exhibits an at least one-axial symmetry about the optical axis 14.

For example, as shown in FIG. 10, a symmetric array of quadratic transmission regions 74 may together form the transmission window 22. The discrete transmission regions 74 are separated from one another by the filter area 20. Of course, the arrangement shown in FIG. 10 can also be reversed. Thus, the filter area 20 may be divided in separate filter regions between which the transmission window 22 is arranged. In such an embodiment, the relatively smaller area of the transmission window 22 compared to the filter area 20 should be still maintained.

In FIG. 11, it is shown that the transmission window 22 and the filter area 20 may be concentric rings arranged alternatingly.

In the following embodiments, the filter system 16, 38 may comprise at least one moveable filter element 80 which is operatively connected to an actuator 82 such as an electric, mechanic or magnetic drive, or a manually operated drive.

The moveable element 80 is configured to be moved from a first position 84 to a second position 86 relative to the optical axis. In the first position 84, the area in the optical path of the transmission window 20 is smaller than in the first position. In the first position, there may even be no transmission window 22 present as exposed to the incident light. Thus, by moving the moveable filter element from the first position 84 to the second position 86, the intensity of the light 8 in the side bands 52 can be increased.

A first embodiment having a moveable filter element 80 is shown in FIGS. 12 and 13. In this embodiment, the moveable filter element 80 is a moveable cover mask 88, which may be translatably and/or as shown in FIGS. 12 and 13 rotatably supported in the medical device 1. In the first position 84, a larger area or all of the transmission window 22 is covered by the cover mask 88. In the second position 86, shown in FIG. 13, a smaller part of the transmission window 22 is covered by the cover mask 88. The cover mask 88 may be an opaque filter or be at least partly transmissive and have band pass characteristics. For example, the cover mask 88 may have the same band pass properties as the filter area 20.

The cover mask 88 may be held in a region 90 beyond the aperture of the filter system 16, 38 for actuation by the actuator 82.

The moveable filter element 80 may, in another embodiment, comprise a filter area 20 which is moved at least partly out of the optical path 12 to create or enlarge the transmission window 22. This is shown in two embodiments in FIGS. 14 and 15, and in FIGS. 16 and 17.

According to the embodiment of FIGS. 14 and 15, the filter system 16, 38 may be split into at least one stationary part 92 comprising part of the filter area 20 and at least one moveable element 80 comprising the remainder of the filter area 20. By moving the moveable filter element 80 away from the stationary filter element 92, a transmission window 22 is created or enlarged in the second position 86 as shown in FIG. 15. At least one of the moveable filter element 80 and the stationary filter element 92 may already be provided with a transmission window to always allow a minimum of light 8 in the side bands 52 to pass the filter system 16, 38. In an alternative embodiment, at least two movable filter elements may be provided which are configured to be moved away from each other to open the transmission window 22.

To allow a gapless closing between the at least one moveable filter element 80 and the at least one stationary filter element 92, a stationary cover 94 may be provided which covers the junction between the two filter elements 80, 92.

In the embodiment of FIGS. 16 and 17, a unitary moveable filter element 80 extends across the whole aperture 62 of the filter system 16, 38. The moveable filter element 80 may, in the first position 84 form a continuous filter area 20 across the filter plane 18. In the second position 86, the moveable element 80 is moved, preferably within the filter plane 18 at least partly out of the aperture so that a transmission window 22 opens.

In the embodiment of FIG. 18, the transmission of the filter area 20 and/or the transmission window 22 varies in a circumferential direction 95 around the optical axis 14. The transmission may, in particular, vary between 0% and 100%. For example, the transmission in the passband of the filter area 20 may be constant across the aperture 62 whereas the transmission in the passband of the transmission window 22 may vary. The variation may be continuous in the circumferential direction 95 or stepwise, e.g. having sectors of preferably equal size, each sector having a different transmission than the neighboring sectors.

Instead of or in addition to the circumferential variation of transmission, the transmission may also vary in a radial direction 96 from the optical axis 14 outwards.

In the embodiment of FIG. 18, the filter area 20 and the transmission window 22 are not discrete areas but overlap each other in that the respective layers which cause the filtering properties of the filter area 20 and the transmission window 22 are put onto one another.

In FIGS. 19-21, the transmission of the filter area 20 or the transmission window 22 is shown unfolded in the circumferential 95 and/or radial 96 direction. Dark areas are areas in which there is no light passing through the respective passband.

In FIG. 19, it is shown that in the circumferential 95 and/or radial 96 direction, the transmission of the filter area 20 may be constant. For example, the filter area may be transmissive in the emission and/or excitation waveband or wavebands of a fluorophore.

According to FIG. 20, the varying transmission is created by a dithering with varying densities. The dithering is done by applying a cover mask 88 to small regions of the aperture. This can be done by applying as a cover mask 88, a layer which is opaque in the passband of the transmission window 22 but translucent in the passband of the band pass filter. Between the individual cover masks 88, transmission regions 74 are situated through which light in the passband may pass. The density of the individual cover masks 88, i.e. the percentage of area covered by the transmission regions 74 between the individual cover masks 88, determines the amount of light in the passband passed through the transmission window 22.

In FIG. 21, a filter system 16, 38 is shown in which the transmission varies continuously in the circumferential 95 and/or radial 96 direction. This can, e.g. be done by varying the thickness of a filter layer which blocks light in the passband of the transmission window.

The type of variation in the circumferential 95 and/or radial 96 direction may depend on the application and be linear and/or non linear.

The filter system 16, 38 which has been explained with reference to FIGS. 18-21, may be varied in that the transmission in the transmission window 22 is constant across the aperture 62, whereas the transmission of the band pass filter varies in the circumferential 95 and/or radial 96 direction. Also, a variation of both the transmission of the band pass filter and the transmission window in the circumferential 95 and/or radial 96 direction is possible.

REFERENCE NUMERALS

1. Medical device
2. Object

3. Tissue
4. Fluorophore
6. Light source
8. Light from light source
10. Diffractive element
12. Optical path
14. Optical axis
16. Illumination filter system
18. Filter plane
20. Filter area
22. Transmission window
24. Band pass filter
26. Substrate
28. Optical system
30. Diffractive element
32. Beam splitter system
34. Viewing System
36. Observation zone
38. Observation filter system
42. Illumination spectrum of light source
44. Passband of filter area of illumination filter system
46. Fluorescence excitation waveband
48. Passband of transmission window
50. Resulting spectrum
52. Side band
54. Fluorescence emission spectrum
56. Passband of filter area of observation filter system
58. Observation spectrum
60. Frame structure
62. Aperture
64. Filter layer
65 Thick arrow
66. Thin arrow
68. First side of substrate
70. Second side of substrate
71 Radial direction
72. Axis of symmetry
74. Transmission region
80. Moveable filter element
82. Actuator
84. First position
86. Second position
88. Cover mask
90. Region outside aperture
92. Stationary part of filter system
94. Stationary cover
95 Circumferential direction
96 Radial direction
I Intensity
λ Wavelength

What is claimed is:

1. A medical device for the observation of a partly fluorescent object such as tissue comprising at least one fluorophore, the fluorophore absorbing light in at least one spectral excitation waveband and emitting fluorescent light in at least one spectral emission waveband, the medical device comprising:
at least one filter system, the filter system being arranged in a filter plane, wherein, in the filter plane, the filter system comprises:
a filter area comprising a band pass filter having at least one passband, the passband comprising at least one of the excitation waveband and the emission waveband, and
a transmission window having a passband which is wider than the passband of the filter area,
wherein the at least one filter system is configured to simultaneously receive light through the filter area and the entire transmission window, and the transmission window is cross-shaped.

2. The medical device according to claim 1, wherein the filter area comprises at least one filter layer which is not present in the transmission window.

3. The medical device according to claim 1, wherein the filter system comprises a light-transmissive substrate on which the band pass filter is arranged as at least one filter layer.

4. The medical device according to claim 1, wherein, in the filter plane, a light flux through the transmission window is less than 1% of a light flux through the filter system.

5. The medical device according to claim 1, wherein the transmission window is symmetric about at least one radial direction passing through an optical axis of the medical device at the filter plane.

6. The medical device according to claim 1, wherein the filter system comprises a substrate, the substrate having two opposing surfaces, wherein the filter area is arranged on each of the two opposing surfaces and the transmission area is arranged on each of the two opposing surfaces.

7. The medical device according to claim 6, wherein the filter area on one of the two opposing surfaces is located opposite the transmission window on the other one of the two opposing surfaces.

8. The medical device according to claim 1, the medical device further comprising a light source, an observation zone, and a viewing system for viewing fluorescent tissue arranged in the observation zone, the light source being configured to emit light in the at least one fluorescence excitation waveband in the direction of the observation zone, wherein the filter system is arranged between at least one of the light source and the observation zone, and the observation zone and the viewing system.

9. The medical device according to claim 8, wherein the at least one filter system comprises:
an illumination filter system arranged between the light source and the observation zone, wherein the passband of the filter area of the illumination filter system comprises the excitation waveband; or
an observation filter system arranged between the observation zone and the viewing system, wherein the passband of the filter area of the observation filter system comprises the emission waveband.

10. The medical device according to claim 9, wherein the at least one filter system comprises the illumination filter system and the observation filter system.

11. The medical device according to claim 1, wherein the at least one passband of the band pass filter comprises a spectral passband which is restricted to one of the fluorescence emission wavebands and the fluorescence excitation wavebands.

12. The medical device according to claim 1, wherein a resulting spectrum of light passed through the at least one filter system in the filter plane includes side bands of the passband of the filter area.

13. The medical device according to claim 1, wherein the passband of the transmission window comprises the visible light range.

14. A filter system for arrangement in a filter plane of a medical device, the filter system comprising:
a filter area comprising a band pass filter having at least one passband, the passband comprising at least one of an excitation waveband and an emission waveband, and a transmission window having a passband which is wider than the passband of the filter area, wherein the filter system is configured to simultaneously receive light through the filter area and the entire transmission window, and the transmission window is cross-shaped.

\* \* \* \* \*